United States Patent
Morisawa

[19]

[11] Patent Number: 5,938,915
[45] Date of Patent: *Aug. 17, 1999

[54] WATER FOR MEDICAL TREATMENT, PRODUCTION METHOD THEREOF, AND DIALYSIS APPARATUS USING WATER FOR MEDICAL TREATMENT AS DIALYSIS LIQUID

[75] Inventor: Shinkatsu Morisawa, Osaka, Japan

[73] Assignee: Nihon Trim Co., Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/675,660

[22] Filed: Jul. 3, 1996

[30] Foreign Application Priority Data

| Jul. 7, 1995 | [JP] | Japan | 7-171902 |
| Jun. 17, 1996 | [JP] | Japan | 8-155647 |

[51] Int. Cl.⁶ .................................................. C02F 1/461
[52] U.S. Cl. .................. 205/464; 205/742; 205/746; 205/747; 204/262; 204/263
[58] Field of Search .................................. 205/464, 742, 205/746, 747; 204/263, 262

[56] References Cited

U.S. PATENT DOCUMENTS

| 4,122,010 | 10/1978 | Riede et al. | 210/90 |
| 4,808,287 | 2/1989 | Hark | 204/182.5 |
| 4,834,888 | 5/1989 | Polaschegg | 210/646 |
| 5,445,722 | 8/1995 | Yamaguti et al. | 204/228 |
| 5,543,030 | 8/1996 | Shiramizu et al. | 205/464 |
| 5,578,193 | 11/1996 | Aoki et al. | 205/747 |

FOREIGN PATENT DOCUMENTS

| 0070346 | 1/1983 | European Pat. Off. . |
| 06193971 | 7/1994 | Japan . |
| 6193971 | 7/1994 | Japan . |
| 7088475 | 4/1995 | Japan . |
| 07185550 | 7/1995 | Japan . |
| 1752315 | 8/1992 | Russian Federation . |
| 1512146 | 5/1978 | United Kingdom . |
| WO89/02709 | 4/1989 | WIPO . |
| WO95/02559 | 1/1995 | WIPO . |

*Primary Examiner*—Arun S. Phasge
*Attorney, Agent, or Firm*—McDermott, Will & Emery

[57] ABSTRACT

A main feature of the present invention is to provide water for medical treatment that can eliminate superoxide anion radicals that trigger various disease. Raw water including at least sodium, potassium, magnesium, and calcium ions is supplied to an eloectrolytic water treatment apparatus comprising a cathode chamber and an anode chamber. A current within the range of 0.16 mA/cm²~3.2 mA/cm² is applied per each pair electrodes and one diaphragm for 0.5 seconds ~5 seconds across a cathode electrode and an anode electrode to electrolyze the raw water. By this method, water for medical treatment is produced that has an oxidation-reduction potential value within the range of −150 mV~0 mV measured against a platinum electrode. The water for medical treatment can remove from the blood of a patient the SAR that causes various disease.

13 Claims, 8 Drawing Sheets

AGE:72 SEX:M

| NO. | FILE | SAMPLE | TIMES | GATE [sec] | TEMP. [C] | TOTAL COUNTS | DARK AV. |
|---|---|---|---|---|---|---|---|
|  | A1-6 | 3180932-1 | 60 | 10 | 36 | 337906 | 569.1 |
| 99 | A1-7 | 3180932-1 | 60 | 10 | 36 | 90734 | 570.2 |
| 100 | A1-82 | 3180932-1 | 60 | 10 | 36 | 87637 | 589.3 |
| 97 | A1-9 | 3180932-1 | 60 | 10 | 36 | 52522 | 555.5 |
| 98 | A1-10 | 3180932-1 | 60 | 10 | 36 | 86037 | 569.0 |

| ml | COUNTS/10secs | | % | ORP (mv) | PH | TEMP °C | A |
|---|---|---|---|---|---|---|---|
| PBS | 317521 | /40-569.1=7368.93 | | | 8.5 | 21 | |
| 1 | 78018 | /40-570.2=1380.25 | ↓ 81.3 | -33 | 8.15 | 21.7 | 0.75 |
| 2 | 75286 | /40-589.3=1292.85 | ↓ 82.5 | -59 | 9.06 | 21.5 | 1 |
| 3 | 40873 | /40-555.5= 466.33 | ↓ 93.7 | -99 | 9.24 | 21.1 | 1.5 |
| 4 | 73287 | /40-569.0=1263.18 | ↓ 82.9 | -111 | 9.40 | 21.1 | 2 |

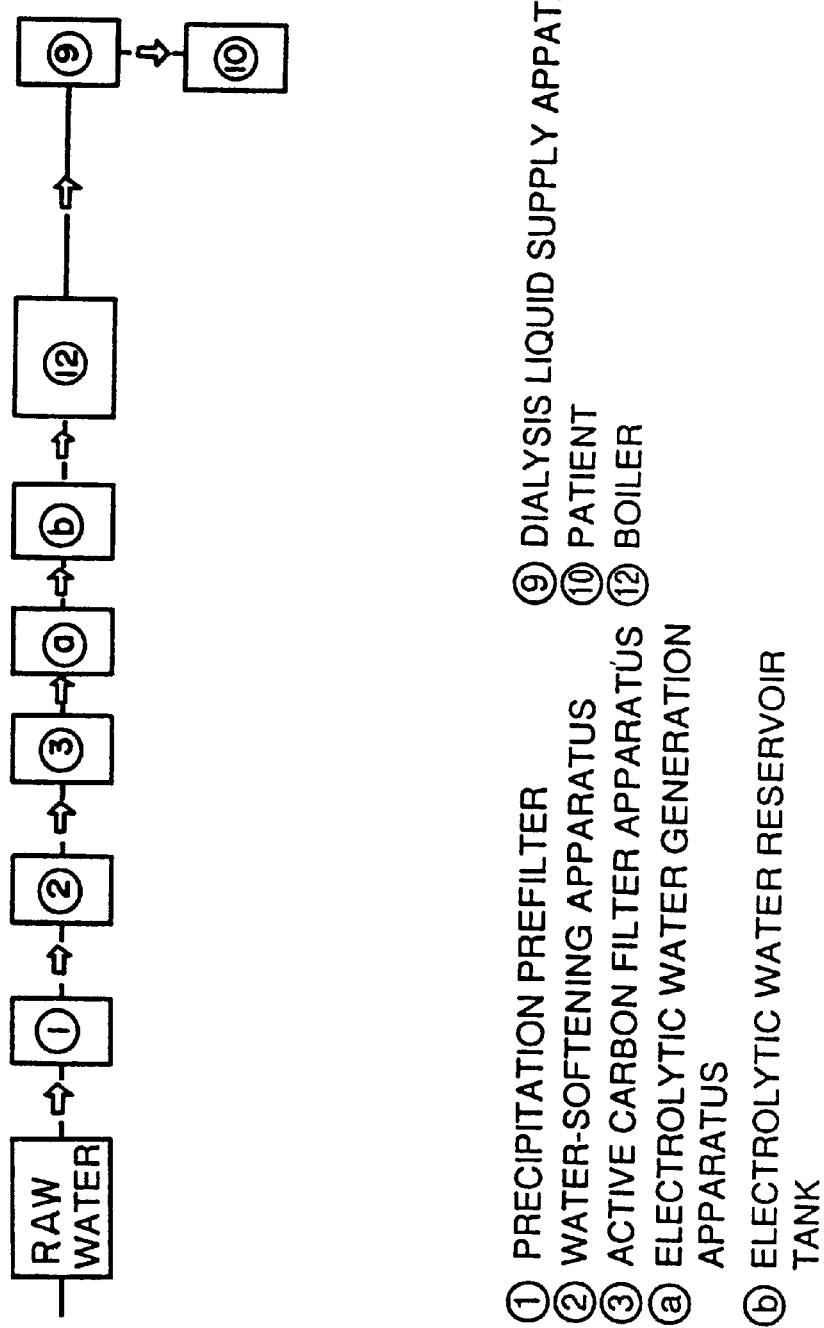

WATER FOR MEDICAL TREATMENT, PRODUCTION METHOD THEREOF, AND DIALYSIS APPARATUS USING WATER FOR MEDICAL TREATMENT AS DIALYSIS LIQUID

BACKGROUND OF THE INVENTION

1. Field of the Invention

The present invention generally relates to water for medical treatment, and more particularly, to water for medical treatment that has potency to eliminate Superoxide Anion Radicals: $O_2^-$. (referred to as "SAR" hereinafter), generated in a living body. The invention also relates to a method of producing such water for medical treatment. Furthermore, the present invention relates to a dialysis apparatus that utilizes such water as dialysis liquid.

2. Description of the Background Art

Significant advances have been seen in the field of modern medicine, and the variety and number of new medicines and drugs available on the market is increasing. Developments in mediomechanical instruments have allowed a more accurate grasp of the functioning of the human body, so that more appropriate treatments can be applied. Many people graduate from medical colleges every year to practice medicine, and advances in the techniques in medical treatment are in progress.

However, the number of people with medical disorders is increasing in spite of such progress in medical science. Accordingly, the total amount of incurred medical fees shows no decrease. It is considered that this is due to the fact that the symptom of the disease is treated nosotropically, and that fundamental therapy is not applied.

Recently, it has been confirmed that SAR generated within the human body act as a trigger of various diseases and illnesses. It is considered that SAR is generated as a result of the oxygen in the blood being subjected to the effect of ischemic re-perfusion, intracorporeal bacteria, uric acid in the blood, fat, and reducible sugar, or by the influence of neutrophil.

There is a great amount of SAR in the blood of individuals with large amounts of uric acid in the blood, fat, and sugar, or with disease. SAR reacts with DNA and the like in the body to induce symptoms and disease such as allergic dermatitis.

A process or method of eliminating this SAR from blood is now drawing the attention of doctors and persons working at medical institutes all over the world.

Conventionally, β-carotene, vitamin C, vitamin E and SOD (Super Oxide-Dismutase) foods are typically known to destroy SAR. However, there is a problem that excessive ingestion thereof will cause reactions such as oxidation effects.

SUMMARY OF THE INVENTION

In view of the foregoing, an object of the present invention is to provide water for medical treatment that has potency to eliminate SAR that becomes the trigger of various disease.

Another object of the present invention is to provide a method of producing such water for medical treatment.

A further object of the present invention is to provide a dialysis apparatus that utilizes such water as a dialysis liquid for medical treatment.

According to an aspect of the present invention, water for medical treatment is obtained which has an oxidation-reduction potential (ORP) value within the range of −150 mV~0 mV measured against a platinum (Pt) electrode. Sterile water having a measured oxidation-reduction potential (ORP) of −68 mV~+55 mV (vs Pt) is obtained by boiling the obtained water.

By electrolyzing water under particular conditions set forth in the following, treated water is obtained at the cathode side (referred to as cathode water hereinafter). The inventors found that the obtained cathode water is rich in electrons ($e^-$) and protons ($H^+$) with potency of destroying SAR generated within the body.

The reaction mechanism of the cathode water for removing SAR is as follows.

$-O_2^-$. (Superoxide Anion Radical)$+e^-+2H^+ \rightarrow H_2O_2$ (hydrogen peroxide)

$H_2O_2+e^- \rightarrow HO^-+HO^-$ $HO^-+e^-+H^+ \rightarrow H_2O$

More specifically, it is believed that SAR which is the cause of various disease is combined with electrons ($e^-$) and protons ($H^+$) included in the cathode water so as to be reduced and converted into $H_2O$ (water) and thus eliminated.

According to another aspect of the present invention, a method of producing water for medical treatment includes the step of providing an electrolytic water treatment apparatus. The electrolytic water treatment apparatus includes a cathode chamber with a cathode and an anode chamber with an anode, the chambers being separated by a diaphragm. Raw water including at least sodium, potassium, magnesium, and calcium ions is supplied to the respective anode and cathode chambers. A current within the range of 0.16 mA/CM²~3.22 mA/cm² per each pair of electrodes and one diaphragm is applied for at least 0.5 second and not more than 5 seconds across the cathode and the anode to electrolyze the raw water. Then, the water within the cathode chamber is extracted. It was found that the cathode water obtained by such a method has the potency to remove SAR.

According to a third aspect of the present invention, apparatus includes an electrolytic water treatment apparatus for electrolyzing water to form cathode water, a filter apparatus for filtering the cathode water supplied from an electrolytic liquid reservoir tank, and a dialysis liquid supply apparatus for supplying cathode water from the filter apparatus as dialysis liquid.

Since the dialysis apparatus of the present aspect includes an electrolytic water treatment apparatus, cathode water that can remove SARs that cause disease can be supplied to the human body as dialysis liquid. Therefore, SAR in the blood of a patient can be removed in addition to the effect of hemodialysis.

According to still another aspect of the present invention, a dialysis apparatus includes an electrolytic water treatment apparatus for electrolyzing water, a boiling apparatus for boiling cathode water fed from the electrolytic water treatment apparatus, and a dialysis liquid supply apparatus for supplying cathode water introduced from the boiling apparatus as dialysis liquid.

Since the dialysis apparatus of the present aspect includes a boiling apparatus, the cathode water can be disinfected to remove the bacteria.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 8 is a diagram showing the concept of a dialysis apparatus according to a third embodiment of the present invention.

DESCRIPTION OF THE PREFERRED EMBODIMENTS

First Embodiment

Figure 1:
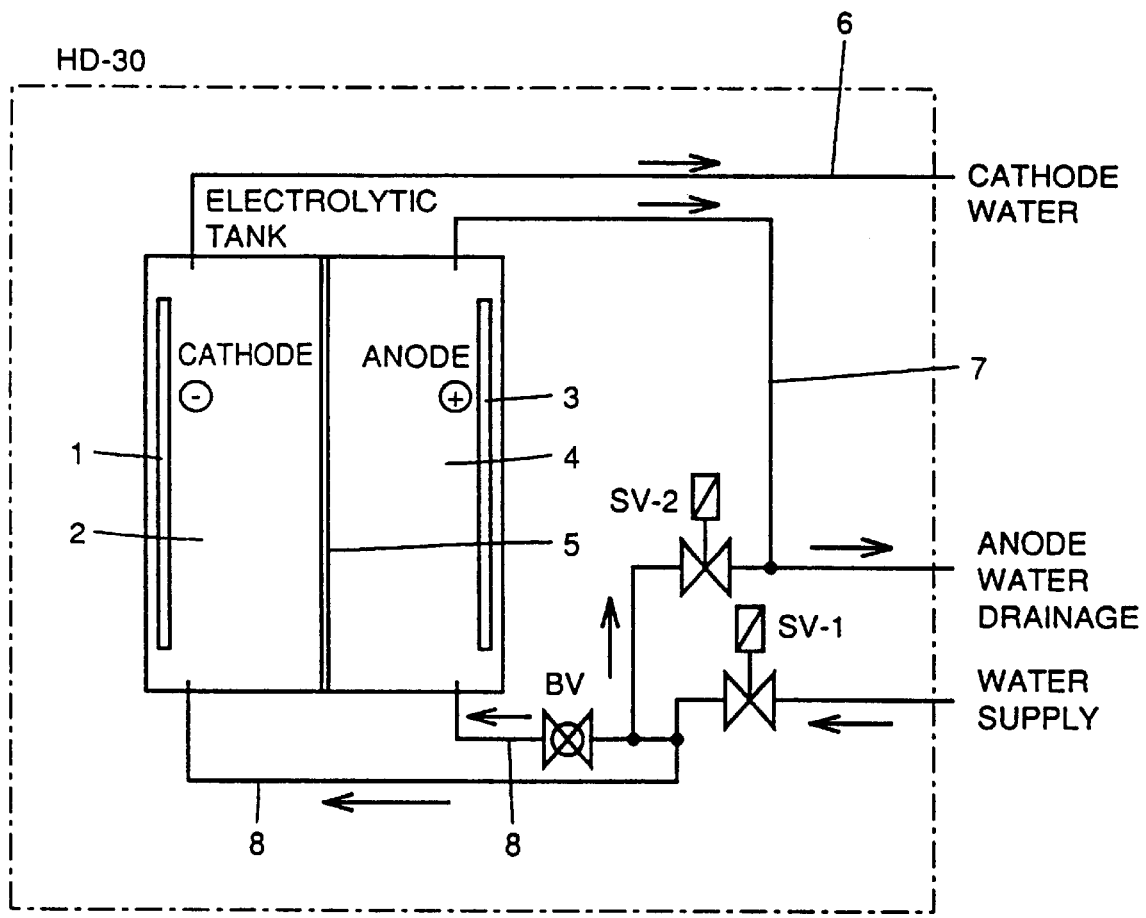
FIG. 1 is a diagram showing the concept of an electrolytic water treatment apparatus for producing water for medical treatment according to the first embodiment of the present invention.

Referring to FIG. 1, an electrolytic water treatment apparatus (HD-30) according to the first embodiment of the present invention includes a cathode chamber with a cathode and an anode chamber with an anode. Cathode chamber is separated from anode chamber by a diaphragm. A cathode liquid outlet pipe 6 from which cathode liquid is drawn out is connected to cathode chamber 2. A drain pipe 7 for discharging anode water is connected to anode chamber 4. Respective feed pipes 8 are connected to cathode and anode chambers 2 and 4 so that raw water including at least sodium, potassium, magnesium, and calcium ions, such as tap water, ground water, or water from a well is supplied.

Raw water such as tap water, ground water, or well water is supplied to cathode chamber 2 and anode chamber 4. A current within the range of 0.16 mA/cm$^2$~3.2 mA/cm$^2$ per each pair of electrodes and one diaphragm is applied across cathode electrode 1 and anode electrode 3 for at least 0.5 second and not more than 5 seconds at room temperature (18° C.~22° C.) to electrolyze the raw water. As a result, cathode water for medical treatment is obtained having the following properties: The oxidation-reduction potential (ORP) indicated in the present specification is measured against a platinum (Pt) electrode by an ORP measuring apparatus (RM-12P) of Toa Denpa Co. Ltd.

pH:8.0~9.5

ORP (oxidation-Reduction Potential): ±0 mV~150 mV

Cathode water of various characteristics was produced using the above-described apparatus and method to study the potency thereof in eliminating SAR from blood.

Figure 2:
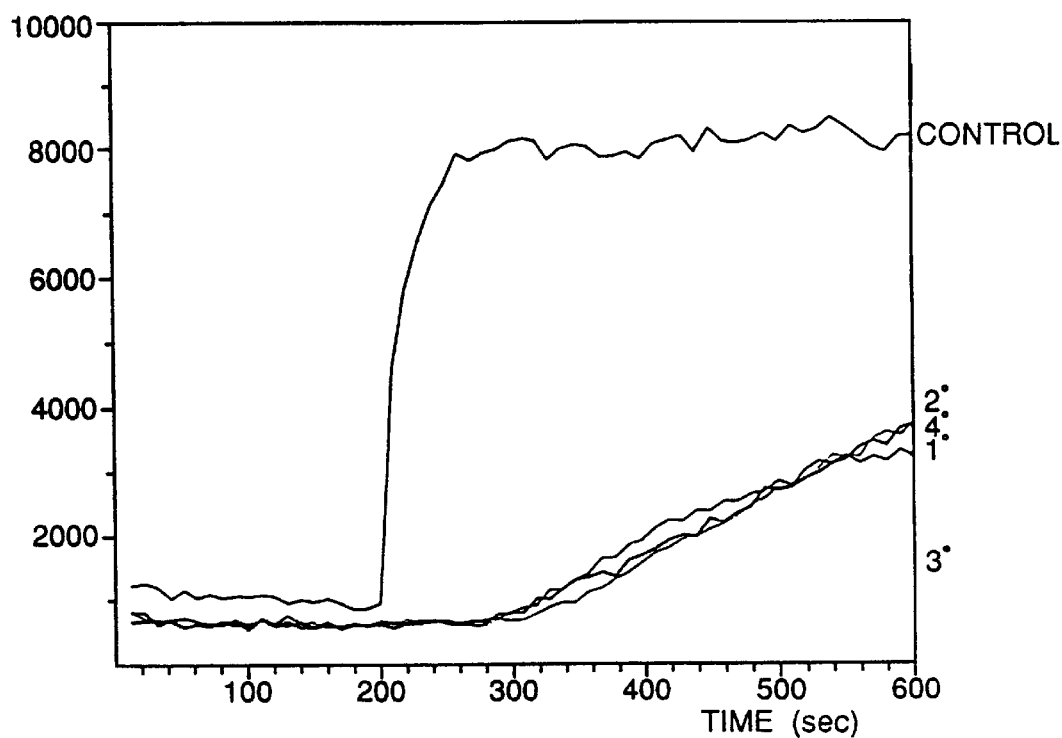
FIG. 2 is a diagram showing the results of tests of the potency of the water for medical treatment according to the first embodiment in eliminating SAR, using blood from a 72-year-old male patient.

The graph of FIG. 2 indicates the amount of SAR in a mixture of blood extracted from a 72-year-old male patient and the above-described cathode water as a function of time. In the graph of FIG. 2, time is plotted along the abscissa, and the amount of SAR in the blood is plotted along the ordinate. The curved line labeled "control" at the right side of the graph shows data when the above-described cathode water is not added. The curved lines labeled 1°, 2°, 3°, and 4° at the right side of the graph indicate data corresponding to the PBS test number.

Figure 3:
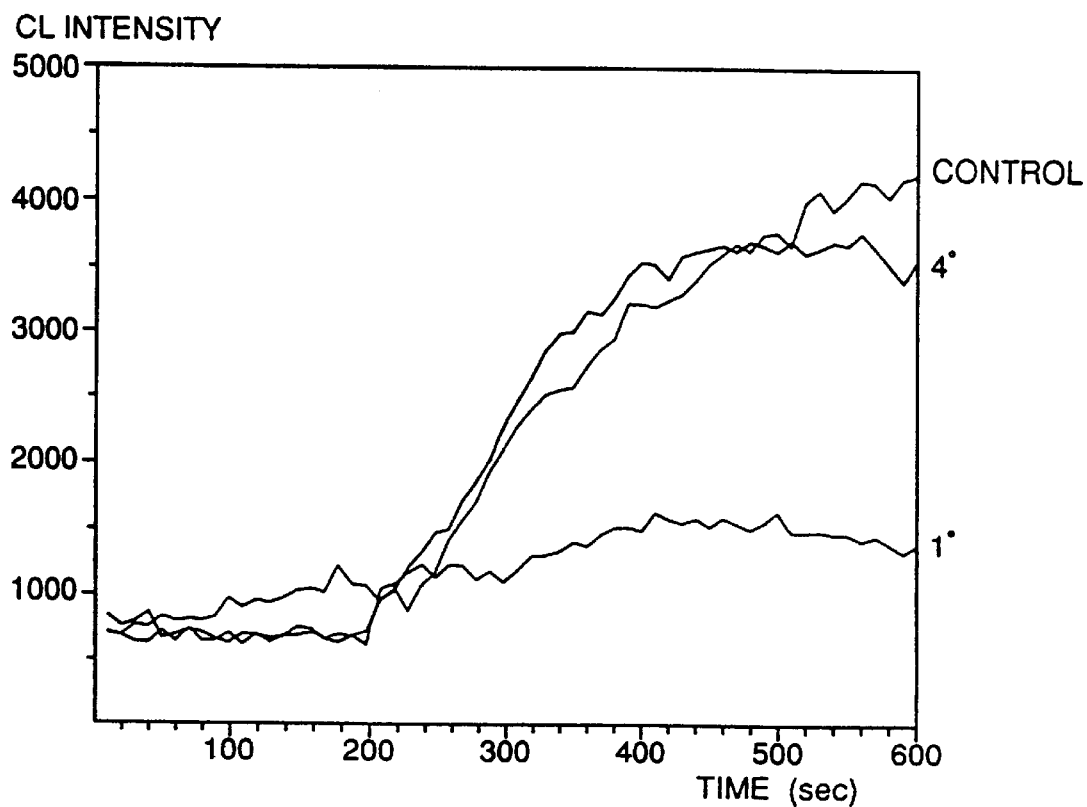
FIG. 3 shows the results of tests of the potency of the water for medical treatment of the first embodiment in eliminating SAR, using the blood of a 38-year-old male patient.

FIG. 3 shows the result of a similar test using blood extracted from a 38-year-old male patient.

Referring to FIGS. 2 and 3, it was found that cathode water having an oxidation-reduction potential (ORP) of −150 mV~0 mV has the greatest potency to remove SAR.

Figure 4:
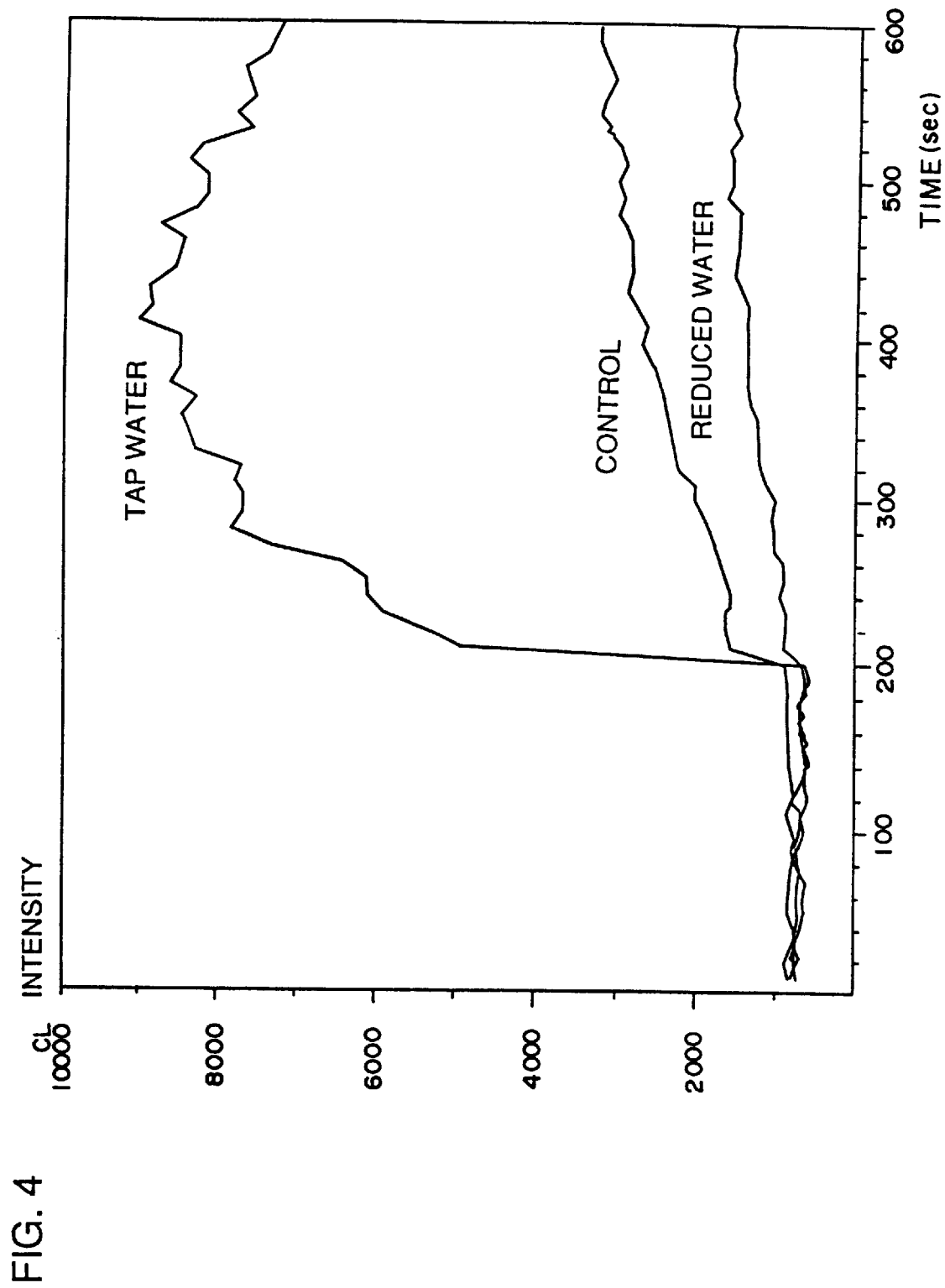
FIG. 4 shows the effect of the water of the present invention using the blood of a patient suffering from acute pancreatitis.

FIG. 4 shows the result of tracing the amount of SAR over time from a mixture of cathode water according to the present invention and blood extracted from a patient suffering from acute pancreatitis. The line labeled "TAP WATER" shows data obtained from a mixture of tap water and the above-described blood, and the line labeled "REDUCED WATER" indicates data obtained from a mixture of cathode water of the present invention and blood. It is seen that the amount of SAR does not decrease with time with tap water. By contrast, for any given elapse of time there is a significantly decreased amount of SAR with the cathode water of the present invention.

The pH of the tap water was 5.8~8.6, and the oxidation-reduction potential (ORP) was +200 mV~+700 mV.

Mode 1

The values of the pH and oxidation-reduction potential (ORP) of the treated water are shown in Table 1 when electrolyzed (current application time 0.5–5 seconds) under various electrolytic currents (A) (generally expressed by current density (mA/cm$^2$)). The current density is shown per one pair of electrodes and one diaphragm. From these experiments, it was found that the current density is preferably 0.16 mA/cm$^2$~3.2 mA/cm$^2$, particularly 0.224 mA/cm$^2$~1.6 mA/cm$^2$.

TABLE 1

| Electrolytic Current (A) | Current Density (mA/cm$^2$) | PH | ORP (mV) |
| --- | --- | --- | --- |
| 0.3 | 1.0 | 8.9 | −43 |
| 1.0 | 3.2 | 9.7 | −142 |
| 1.5 | 4.9 | 10.1 | −188 |
| 2.0 | 6.5 | 10.4 | −210 |

Mode 2

An experiment was carried out wherein the cathode water obtained as described above was boiled to kill bacteria in the cathode water. It was found that cathode water subjected to boiling does not lose the potency to eliminate SAR.

Specifically, two types of cathode water having an oxidation-reduction potential of 0 mV and −150 mV were boiled. The water was boiled for five minutes, and then cooled for twenty minutes. The respective measured values of pH and ORP are shown in the following Table 2 and Table 3.

Table 2 shows the data measured using water of Kochi city. Table 3 shows the data measured using water of Kyoto city. It was found that sterile water for medical treatment having an oxidation-reduction potential (ORP) value within the range of −68 mV~+55 mV is obtained by boiling the cathode water.

TABLE 2

|  | Before Boiling | After Boiling |
| --- | --- | --- |
| pH | 9.26 | 9.64 |
| ORP | 0 mV | +55 mV |
| pH | 11.2 | 10.7 |
| ORP | −150 mV | −33 mV |

TABLE 3

|  | Before Boiling | After Boiling |
| --- | --- | --- |
| pH | 8.7 | 9.0 |
| ORP | −10 mV | +21 mV |
| pH | 9.8 | 9.9 |
| ORP | −172 mV | −68 mV |

The cathode water (before and after boiling) obtained in the above-described manner was stable for more than 80 hours. It can be preserved without degradation in properties for about one year if sealed.

Second Embodiment

The second embodiment of the present invention relates to an improved dialysis apparatus wherein cathode water having the above-described properties can be used as a dialysis liquid.

First, a conventional dialysis apparatus will be described with reference to FIG. 5.

Tap water (raw water) is passed through a precipitation prefilter 1 to remove particles. It is then fed to a water-softening apparatus 2 to soften the water. Then, chlorine.chloramine.endotoxin is removed by an active carbon filter apparatus 3. The water is then passed through a UV germicidal lamp 4 and then fed to a reverse osmosis apparatus 5. Only approximately one-half of the water fed into reverse osmosis apparatus 5 under pressurization passes through. The remaining half is processed as drainage. The water which passes through is sterile purified water which is then stored in an RO water tank 6. The water is sterilized with a UV germicidal lamp 7 and then conducted through a millipore filter 8 and fed into a dialysis liquid supply apparatus 9. Here, the processed water is mixed with an undiluted solution of sodium hydrogen carbonate and undiluted electrolytic solution at a predetermined ratio, and passed through a deaerator apparatus to be supplied to a patient 10 as dialysis liquid.

Hemodialysis carried out by a dialysis apparatus is a treatment comprising substance exchange of the patient's intracorporeal-circulated blood and dialysis liquid (one type of electrolytic liquid) in a dialyzator via a membrane to remove and supply solute to the blood and to remove excessive water. A patient suffering from chronic renal insufficiency is subjected to hemodialysis approximately 3 times a week, each time taking about 4 hours. Since the flow rate of the dialysis liquid supplied to the dialyzator is normally 500 ml/minute, the amount of dialysis liquid used in one treatment is 500 ml×240 minutes=120,000 ml=120 l per patient. Since this hemodialysis treatment requires a great amount of water, the content of the water used in hemodialysis affects the patient greatly. The present embodiment is directed to this fact, and relates to utilizing the above—described cathode water of particular composition in a dialysis apparatus.

Figure 6:
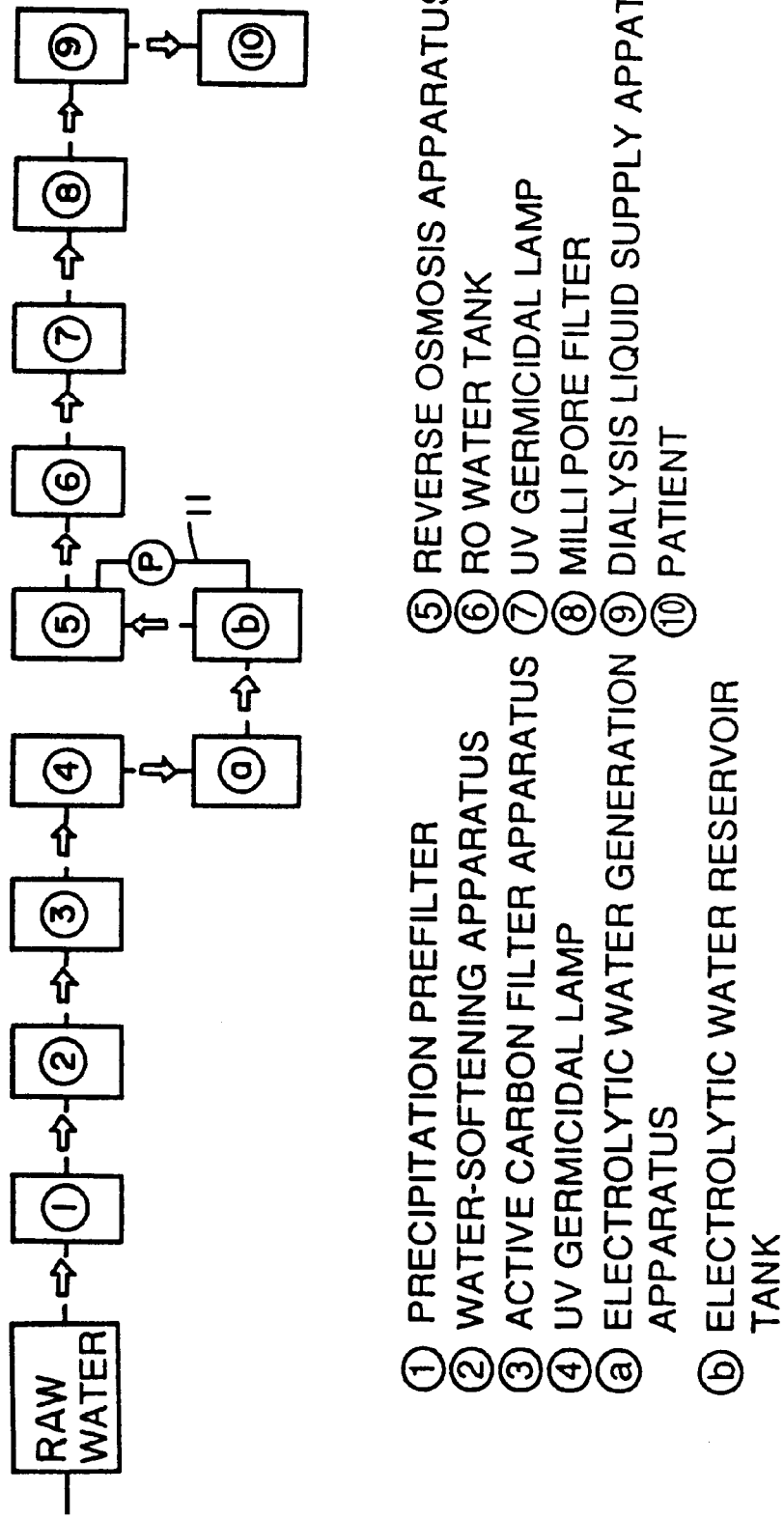
FIG. 6 is a diagram showing the concept of the dialysis apparatus of the second embodiment.

FIG. 6 shows a dialysis apparatus according to the second embodiment of the present invention.

Figure 5:
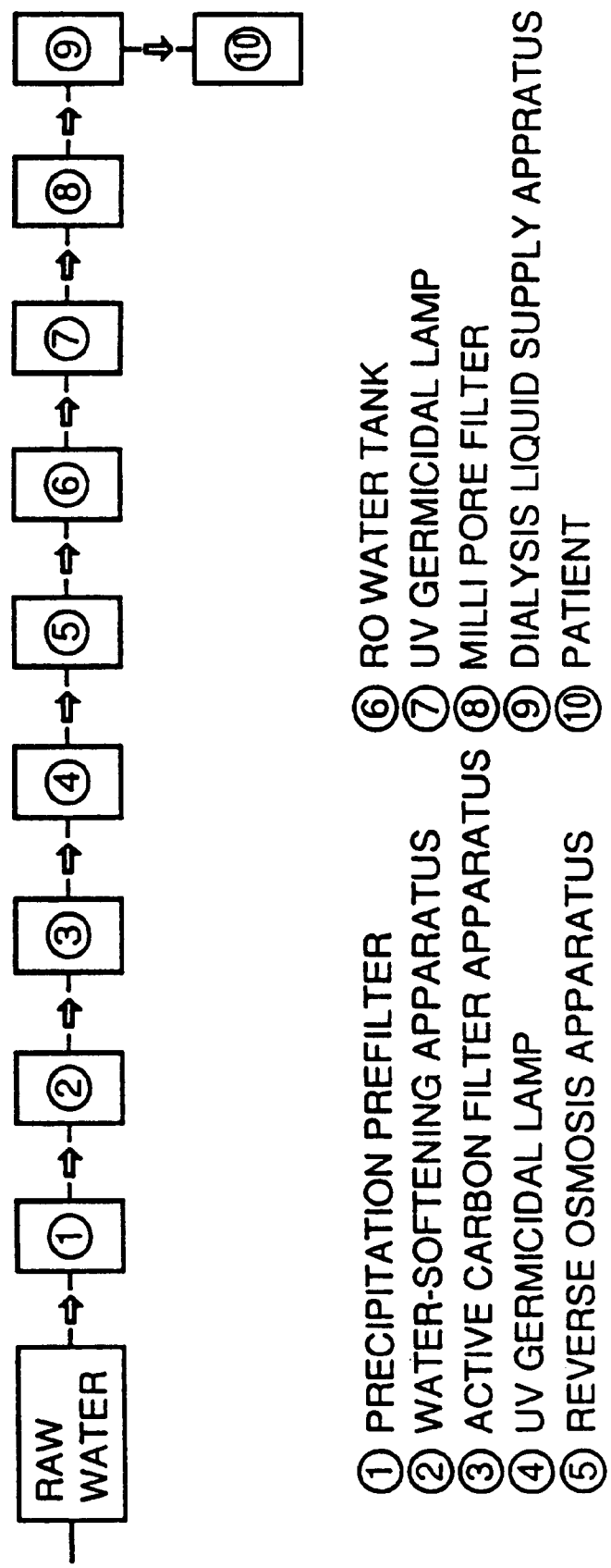
FIG. 5 is a diagram showing the concept of a conventional dialysis apparatus as an aid in describing a dialysis apparatus according to a second embodiment of the present invention.

The dialysis apparatus of the second embodiment differs from the conventional dialysis apparatus of FIG. 5 in that an electrolytic water treatment apparatus (a) and an electrolytic water reservoir tank (b) are provided between UV germicidal lamp 4 and reverse osmosis apparatus 5.

Tap water (raw water) is passed through precipitation prefilter 1 to have particles removed therefrom. Next, the water is softened by water-softening apparatus 2 and supplied to active carbon filtering apparatus 3 to remove chlorine.chloramine.endotoxin. Then, the water is passed through UV germicidal lamp 4. The sterilized water is fed to electrolytic water treatment apparatus (a) to be electrolyzed. Cathode water obtained by electrolysis is stored in electrolytic water reservoir tank (b) and fed to reverse osmosis apparatus 5. Here, half of the feed water passes through, and the remaining water flows through a feedback conduit 11 provided between reverse osmosis apparatus 5 and electrolytic water reservoir tank (b) to be returned to electrolytic water reservoir tank (b) by a pump P. The water which passes through reverse osmosis apparatus 5 is substantially purified water with no germs. This water is stored in RO water tank 6 and then sent to dialysis liquid supply apparatus 9 via UV germicidal lamp 7 and millipore filter 8. The processed water is combined with an undiluted solution of sodium hydrogen carbonate and an electrolytic undiluted solution at a predetermined ratio. The mixture is passed through a deaerator to be supplied to patient 10 as dialysis liquid.

Figure 7:
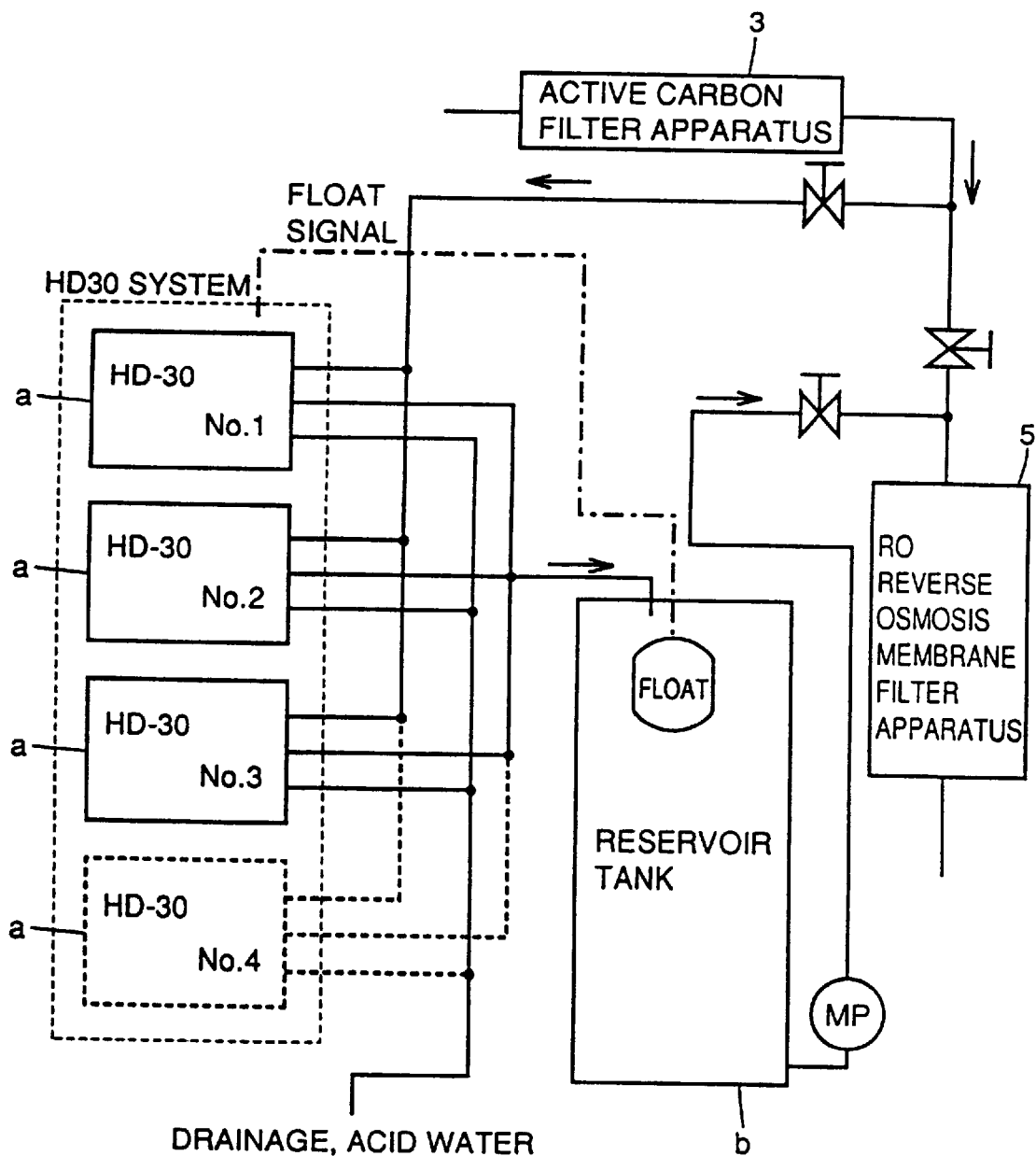
FIG. 7 shows a characterizing portion of the dialysis apparatus of the second embodiment in detail.

FIG. 7 shows the details of active carbon filter apparatus 3, electrolytic water treatment apparatus (a) (HD-30), electrolytic water reservoir tank (b), and reverse osmosis apparatus 5 shown in FIG. 6.

The present invention is not limited to four electrolytic water generators (HD-30) shown in the figure.

Also, the invention is not limited to the present dialysis apparatus wherein an electrolytic liquid reservoir tank is provided. An electrolytic water reservoir tank is not necessarily required, and water can be supplied directly to reverse osmosis apparatus 5 from electrolytic water treatment apparatus (a).

In the present embodiment, a reverse osmosis filtering apparatus is shown as an apparatus for filtering cathode water. Alternatively, cathode water can be filtered with a hollow fiber membrane filter.

According to the dialysis apparatus of the second embodiment, SAR in the blood of a patient can be removed in addition to the effect of a conventional hemodialysis treatment. The frequency of being subjected to dialysis for a patient suffering from chronic renal insufficiency is reduced, thus shortening the time required for the treatment. Consequently, there is an advantage in that the time during which the patient is bound to the dialysis apparatus can be shortened.

Third Embodiment

A dialysis apparatus according to a third embodiment of the present invention shown in FIG. 8 is similar to the dialysis apparatus of FIG. 6 except for the following points. Like or corresponding components are represented by the same reference characters, and their description will not be repeated.

More specifically, the dialysis apparatus according to the third embodiment of the present invention includes a boiler means 12, and does not include sterilizing means such as a UV germicidal lamp, a reverse osmosis apparatus, an RO liquid tank, a UV germicidal lamp, and a millipore filter. Water introduced from electrolytic water reservoir tank (b) to boiler 12 is boiled and sterilized. Then, the sterile water is fed to dialysis liquid supply apparatus 9 to be supplied to patient 10. By substituting a sterilization means such as a boiler 12, the cost and burden of maintenance are reduced in contrast to the case where sterilization means such as a UV germicidal lamp is used.

The present invention is not limited to the above-described first to third embodiments in which the water for medical treatment of the above-described property is used for cleaning blood, and can be used as Ringer's solution and cleaning water used during operations.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of medical treatments, comprising the steps of:

providing an electrolytic water treatment apparatus including a cathode chamber with a cathode and an anode chamber with an anode, said chambers separated by a diaphragm, introducing raw water including at least sodium, potassium, magnesium, and calcium ions into said cathode chamber and said anode chamber, applying a current within a range of 0.16 mA/cm$^2$~3.2 mA/cm$^2$ per each pair of electrodes and one diaphragm across said cathode and anode for 0.5 seconds to 5 seconds for electrolyzing said raw water, extracting electrolyzed water from said cathode chamber, and directly administering the extracted electrolyzed water to the blood of a patient to lower superoxide anion radicals generated in the patient's body.

2. The method according to claim 1, wherein said current is within a range of 0.224 mA/cm$^2$~1.6 mA/cm$^2$.

3. The method according to claim 1, further comprising the step of boiling said extracted electrolyzed water.

4. A dialysis apparatus comprising:

electrolytic water treatment means for electrolyzing water, filter means for filtering cathode water obtained from said electrolytic water treatment means, dialysis liquid supply means for supplying the cathode water from said filter means as dialysis liquid, and dialysis means for dialyzing a patient's internal-circulated blood against said dialysis liquid.

5. The dialysis apparatus according to claim 4, wherein said electrolytic water treatment means is adapted for supplying cathode water having an oxidation-reduction potential value within a range of −150 mV~0 mV measured against a platinum electrode.

6. The dialysis apparatus according to claim 4, wherein said electrolytic water treatment means is adapted for supplying cathode water containing electrons and protons.

7. The dialysis apparatus according to claim 6, wherein said electrolytic water treatment means is adapted for supplying cathode water containing a sufficient amount of said electrons and protons to convert $O_2^{-}\bullet$ into $H_2O$ by the following reaction mechanism:

$O_2^{-}\bullet + e^- + 2H^+ \rightarrow H_2O_2$ $H_2O_2 + e^- \rightarrow HO\bullet + HO^-$ $HO\bullet + e^- + H^+ \rightarrow H_2O$.

8. The dialysis apparatus according to claim 4, further comprising drain means provided at said filter means for draining excessive cathode water supplied from said electrolytic water treatment means.

9. The dialysis apparatus according to claim 8, wherein said drain means comprises a feedback conduit provided between said electrolytic water treatment means and said filter means for returning said excessive cathode water from said filter means back to said electrolytic water treatment means, and a pump provided within said feedback conduit.

10. A dialysis apparatus comprising:

electrolytic water treatment means for electrolyzing water, boiling means for boiling cathode water from said electrolytic water treatment means, dialysis liquid supply means for supplying the cathode water from said boiling means as dialysis liquid, and dialysis means for dialyzing a patient's internal-circulated blood against said dialysis liquid.

11. The dialysis apparatus according to claim 10, wherein said electrolytic water treatment means is adapted for supplying cathode water having an oxidation-reduction potential value within a range of −150 mV~0 mV measured against a platinum electrode.

12. The dialysis apparatus according to claim 10, wherein said electrolytic water treatment apparatus is adapted for supplying cathode water containing electrons and protons.

13. The dialysis apparatus according to claim 12, wherein said electrolytic water treatment apparatus is adapted for supplying cathode water containing a sufficient amount of electrons and protons to change $O_2^{-}\bullet$ into $H_2O$ by the following reaction mechanism:

$O_2^{-}\bullet + e^- + 2H^+ \rightarrow H_2O_2$ $H_2O_2 + e^- \rightarrow HO\bullet + HO^-$ $HO\bullet + e^- + H^+ \rightarrow H_2O$.

* * * * *